US011052233B2

(12) United States Patent
Wolkenstoerfer et al.

(10) Patent No.: US 11,052,233 B2
(45) Date of Patent: Jul. 6, 2021

(54) TUBE FOR A MEDICAL CONTAINER

(71) Applicants: N.V. Nutricia, HM Zoetermeer (NL); Raumedic AG, Helmbrechts (DE)

(72) Inventors: Reinhold Wolkenstoerfer, Neunkirchen (DE); Ralf Ziembinski, Koeditz-Brunnenthal (DE)

(73) Assignees: N.V. Nutricia, Zoetermeer (NL); RaumedicAG, Helmsbrechts (DE)

( * ) Notice: Subject to any disclaimer, the term of this patent is extended or adjusted under 35 U.S.C. 154(b) by 0 days.

(21) Appl. No.: 15/783,821

(22) Filed: Oct. 13, 2017

(65) Prior Publication Data

US 2018/0117295 A1     May 3, 2018

Related U.S. Application Data

(63) Continuation of application No. PCT/EP2016/056912, filed on Mar. 30, 2016.

(30) Foreign Application Priority Data

Apr. 13, 2015 (WO) .................. PCT/EP2015/057959

(51) Int. Cl.
*A61M 5/32* (2006.01)
*A61M 39/08* (2006.01)
(Continued)

(52) U.S. Cl.
CPC ........... *A61M 39/08* (2013.01); *A61L 29/041* (2013.01); *B32B 1/02* (2013.01); *B32B 1/08* (2013.01);
(Continued)

(58) Field of Classification Search
CPC ....... B32B 1/08; B32B 27/08; B32B 2367/00; B32B 2307/412; B32B 2307/306;
(Continued)

(56) References Cited

U.S. PATENT DOCUMENTS 4,465,487 A * 8/1984 Nakamura ................ A61J 1/10
                                                        604/408
5,733,619 A   3/1998 Patel et al.
(Continued)

FOREIGN PATENT DOCUMENTS

BY          5743 C1   12/2003
CN    202733209 U     2/2013
(Continued)

OTHER PUBLICATIONS

European Patent Office, International Search Report, PCT/EP2016/056912, N.V. Nutricia, dated May 4, 2016, 3 pages.
(Continued)

*Primary Examiner* — Ellen S Hock
(74) *Attorney, Agent, or Firm* — Taft Stettinius & Hollister LLP

(57) ABSTRACT

A tube for a medical container has a tube wall which consists of at least two layers. According to the invention, at least one layer contains a styrene-containing thermoplastic polymer (S-TPE), in particular a styrene-butadiene block copolymer (SBC) or a copolyester, a copolyester ether or a cyclic olefin copolyester. The at least one other layer contains ethylene-vinyl acetate copolymer (EVA), preferably with a vinyl acetate (VA) portion in the ethylene-vinyl acetate copolymer of from 10% to 30%, preferably 14% to 28%. The EVA can be mixed with a thermoplastic polybutene and/or SEBS to improve the tube properties. The tube wall can have a two-layer structure with an inner or an outer layer which contains the S-TPE, copolyester, copolyester ether or cyclic olefin copolyester, or a three-layer structure with an outer and inner layer containing the S-TPE or copolyester or copolyester ether.

20 Claims, 3 Drawing Sheets

Figure 1:
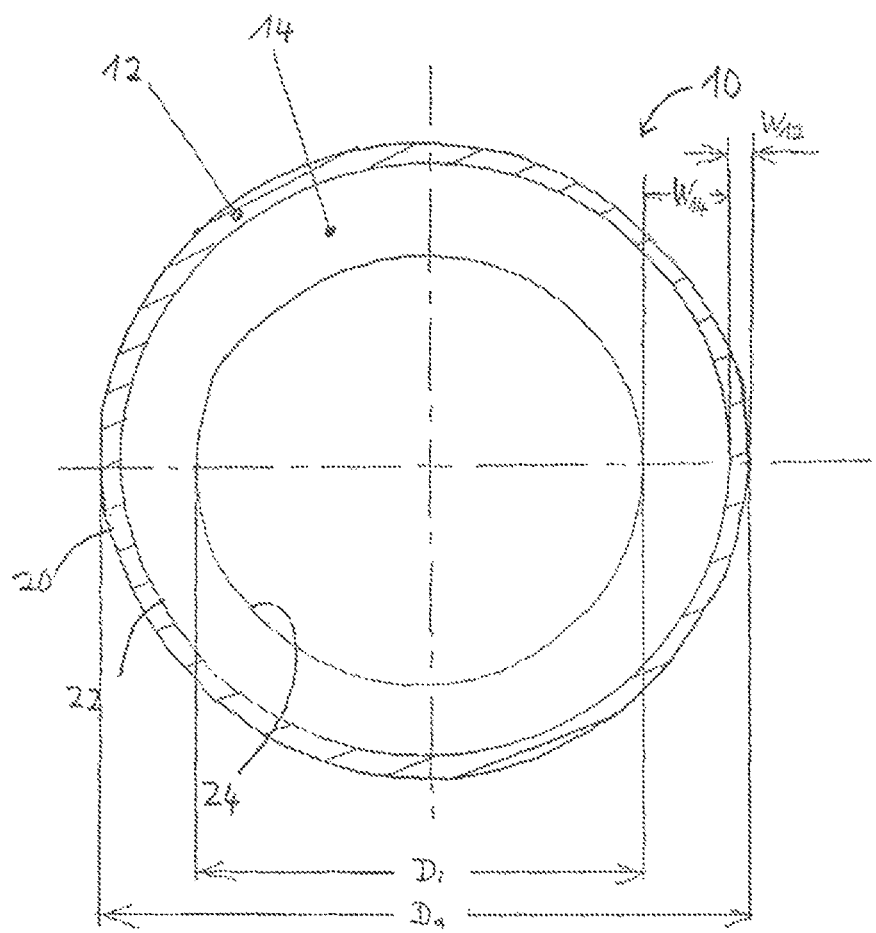

(51) Int. Cl.
*A61L 29/04* (2006.01)
*B32B 27/08* (2006.01)
*B32B 27/30* (2006.01)
*B32B 1/08* (2006.01)
*B32B 1/02* (2006.01)
*B32B 27/32* (2006.01)

(52) U.S. Cl.
CPC ............ *B32B 27/08* (2013.01); *B32B 27/302* (2013.01); *B32B 27/306* (2013.01); *B32B 27/308* (2013.01); *B32B 27/325* (2013.01); *B32B 2270/00* (2013.01); *B32B 2274/00* (2013.01); *B32B 2307/306* (2013.01); *B32B 2307/412* (2013.01); *B32B 2307/714* (2013.01); *B32B 2307/732* (2013.01); *B32B 2435/02* (2013.01); *B32B 2535/00* (2013.01); *B32B 2597/00* (2013.01)

(58) Field of Classification Search
CPC . B32B 2270/00; B32B 27/325; B32B 27/308; B32B 27/306; B32B 27/302; A61M 39/08; A61L 29/041
USPC ............................................. 428/36.91, 36.9
See application file for complete search history.

(56) References Cited

U.S. PATENT DOCUMENTS

| | | | |
|---|---|---|---|
| 8,178,647 B2 | 5/2012 | Hawkins et al. | |
| 2009/0087606 A1 | 4/2009 | Julien | |
| 2010/0055367 A1 | 3/2010 | Ohigawa | |
| 2014/0037880 A1* | 2/2014 | Siddhamalli | B32B 1/08 428/36.91 |
| 2015/0075665 A1 | 3/2015 | Henry | |

FOREIGN PATENT DOCUMENTS

| | | |
|---|---|---|
| DE | 19504414 C2 | 8/1996 |
| EA | 013611 B1 | 6/2010 |
| EP | 355711 A1 | 2/1990 |
| EP | 0729761 A2 | 9/1996 |
| EP | 2620168 A1 | 7/2013 |
| RU | 2277476 C2 | 6/2006 |
| RU | 2447996 C2 | 4/2012 |
| WO | 9323093 A1 | 11/1993 |
| WO | 0076564 A1 | 12/2000 |
| WO | 2008127046 A1 | 10/2008 |
| WO | 2012037462 A2 | 3/2012 |
| WO | 2014018877 A1 | 1/2014 |

OTHER PUBLICATIONS

BASF Corporation, Product Datasheet "Styroflex 2G 66," dated Oct. 2008 (2 pages).
Eastman Chemical Company, Product Datasheet "Tritan TM Copolyester MX710," dated Nov. 11, 2014 (15 pages).
Eastman Chemical Company, Brochure titled "Neostar Elastomer" including "Ecdel TM Elastomer 9966" and "Ecdel TM Elastomer 9967," dated Sep. 2017 (30 pages).
Topas Advanced Ploymers Brochure titled "TOPAS Elastomer," dated Oct. 2010 (18 pages).
Nederlands Normalisatie-Institute, publications provided by Nutricia Medical Devices—Europäische Norm EN 1618/1615, No. 1618 titled "Catheters other than Intravascular Catheters—Test Methods for Common Properties," published Mar. 1997 (16 pages) and No. 1615 titled "Enteral Feeding Catheters and Enteral Giving Sets for Single Use and their Connectors," published Nov. 2000 (18 pages).
Drishti Polytech, Product Specification sheet titled "Koattro—C4 Elastomer," dated Nov. 11, 2014 (2 pages).
Basf Global, Product Datasheet titled "Eigenschaften von Styroflex (SBS Blockpolymer)," dated Dec. 9, 2001 (2 pages).
Wikipedia definition of "Copolyester" Nov. 2017.
Eastman Chemical Company, Brochure for Eastman Tritan Copolyester titled "Redefining the balance between Processability and Chemical Resistance," dated Feb. 2009 (12 pages).
Eastman Chemical Company, Brochure for Eastman Specialty Plastics titled "Lipid and Isopropanol Resistance of Eastman Polymers in Medical Devices," dated Sep. 2007 (4 pages).
Eastman Chemical Company, Brochure titled "Eastman Tritan TM Copolyester for Renal Treatment Device Applications," dated Feb. 2010 (4 pages).
Eastman Chemical Company, Product Regulatory Information, Data and Material Sheets for "Eastman Tritan TM Copolyester MX731," dated Mar. 23, 2011 (15 pages).
European Patent Office, Written Opinion, PCT/EP2016/056912, N.V. Nutricia, dated May 13, 2016, 4 pages.
The Federal Institute of Industrial Property, Search Report, 2017135409/ 04(061775), N.V. Nutricia, dated Jan. 23, 2019, 2 pages.

\* cited by examiner

TUBE FOR A MEDICAL CONTAINER

FIELD OF THE INVENTION

The present invention relates to a tube for a medical container according to the preamble of claim 1, in particular to a tube with a tube wall which consists of at least two layers.

A tube for a medical container, also called a medical tube below, is characterized in that the tube is flexible, soft and transparent and that it does not kink when guided around curves or when bent and block the lumen of the tube at the kinking point. Another important attribute of a medical tube is that the tube springs back reliably and safely elastically after it has been compressed. The latter attribute is to be equated with good elasticity or good recovery behavior and is also described as "having a good snap". This attribute is important in particular when using the medical tube in interaction with tube-deforming pump systems. An application area of such tubes is the parenteral or enteral nutrition of patients in particular.

PRIOR ART

Medical tubes that comprise a substantially homogeneous tube wall of polyvinyl chloride (PVC) with plasticizers embedded therein have been in widespread use for many decades. Advantages of these tubes made from PVC with plasticizers are the economical manufacture due to the easy availability of the starting material and the fact that these tubes are transparent and have good recovery behavior. Without the addition of plasticizers, the polyvinyl chloride would be too hard as such for use in a medical tube. Disadvantages of such tubes are that in recent years the plasticizers normally used for the PVC have come under suspicion of being hazardous to health. Another disadvantage of these tubes is that hydrochloric acid is released when they are disposed of by incineration, and also dioxins depending on the thermal conditions. This disposal is thus not environmentally compatible as such and must take place in specially shielded conditions, which increases the cost of disposal.

In the context of further development to provide tubes that are environmentally compatible in disposal and contain no substances hazardous to health, in particular no carcinogenic substances, tubes were proposed in EP 0 355 711 with a tube wall consisting of homogeneous ethylene-vinyl acetate copolymer (EVA) with a vinyl acetate (VA) portion of 12 to 28%. These so-called monotubes of EVA as an alternative to tubes of PVC are transparent, soft and flexible and have good recovery behavior (a good snap). These monotubes of EVA can also be connected well to medical containers if these containers or the extension pieces for the tube that are fastened to them are likewise produced from ethylene-vinyl acetate. The medical tube can then be easily welded to the container or its extension piece. A disadvantage of monotubes made from EVA is that the EVA cannot be bonded, in particular not bonded using commercially available solvents, with materials normally used in medical containers on account of its chemical inertness. These materials include, for instance, the materials used in extension pieces or connectors, which typically comprise acrylonitrile butadiene styrene (ABS), polycarbonate (PC), polyvinyl chloride (PVC), polymethyl methacrylate (PMMA), copolyester, copolyester ether, thermoplastic polyurethane (TPU) or combinations of these substances. To provide medical tubes that can be bonded well with said materials, medical tubes were proposed in DE 195 04 414 of which the tube wall comprises a composition of at least two layers, wherein an outer layer contains ethylene-vinyl acetate (EVA) and an inner layer contains polyurethane (PU). In these two-layer tubes, the inner layer of polyurethane serves as an adhesive element that enables the proposed tube to be bonded well by pushing it onto a connector of a medical container, which connector is manufactured from one of the aforesaid typically used materials and is formed with a conical shape. A disadvantage of the two-layer tubes with a polyurethane layer as adhesive layer is that this tube is rather expensive to manufacture compared with traditional tubes of PVC with plasticizers. Another disadvantage is that this tube is only suitable for connection to a connector formed with a conical shape by pushing it onto this connector.

U.S. Pat. No. 8,178,647 B2 describes medical multilayer tubes, which include an outer layer with Ecdel 9966, a middle layer of EVA and an inner layer of LDPE. Although these tubes have good adhesive properties and can be joined to connectors, they are too hard and are thus poorly suited for use as medical tubes.

In conventional joining technology of tubes and medical containers, two types of connection are generally known. According to a first type, the container has a connector formed as a mandrel or with a conical shape, onto which a medical tube can be pushed. When pushing the tube onto the cone-shaped connector, a solvent is typically used as a lubricant, and the tube to be pushed on has an internal surface layer that can be dissolved by the solvent. The adhesion of the tube to or its bonding with the cone-shaped connector can be improved by elongating the tube after it has been pushed on. By elongating the tube, the tube shrinks with regard to its diameter, so that an inwardly directed pressure on the cone-shaped connector increases. According to a second type of a connection between a medical container and a medical tube, the container has a connector formed as an adaptor piece and the tube can be inserted into an opening in the adaptor piece on the distal side. With this second type it is essential that a good bonding or seal is achieved between the outer surface of the tube and the inner surface of the adaptor piece of the connector. Since no elongation of the tube occurs with this type of connection, it is necessary that the outside of the tube has a good solubility for a solvent or adhesive and a connection is created thereby to the material on the inside of the adaptor piece.

The object of the present invention is to provide a tube for a medical container that has an improved connectability, in particular bonding capability, and is flexible.

To achieve the object, a tube for a medical container is proposed, wherein the tube has a tube wall that consists of at least two layers. According to the invention, at least one layer contains a styrene-containing thermoplastic polymer (S-TPE), a copolyester, a copolyester ether or a cyclic olefin copolymer (COC).

Thermoplastic elastomers (linear elastomers; TPE) are plastics that behave in a manner comparable to the classic elastomers at room temperature, but which can be deformed plastically when heat is applied and which thus demonstrate thermoplastic behavior. Thermoplastic elastomers are materials in which elastic polymer chains are integrated into thermoplastic material. Although no chemical cross-linking by time-consuming vulcanization at high temperatures is necessary, as with the elastomers, the parts produced still have rubber-elastic properties on account of their particular molecular structure.

Block copolymers and elastomer alloys are often distinguished by the inner structure of TPEs. Block copolymers possess hard and soft segments within a molecule, such as e.g. styrene-butadiene-styrene block copolymers (SBS). Elastomer alloys, on the other hand, are blends, hence physical mixtures of finished polymers. Through different mixing ratios and additives a material can be obtained with desirable properties, such as e.g. polyolefin elastomer from polypropylene and natural rubber. Depending on the quantity ratio, the hardness can be adjusted in a wide range.

Styrene-containing thermoplastic polymers (S-TPE) can be formed in principle as stated above as block copolymers or elastomer alloys.

The styrene-containing thermoplastic polymer (S-TPE) can be a styrene-butadiene block copolymer (SBC) in a preferred embodiment. One example of such an SBC is, as described below, polystyrene-butadiene-polystyrene (SBS). SBCs are easily and cheaply available commercially, for example from the company BASF under the brand name Styroflex®, wherein the Styroflex with the product designation 2G 66 is preferably used. In English the term "SBC" is commonly used for these, while the terms "SBS" and "SEBS" are common in German.

In the present invention, styrene block copolymers in particular are preferable, wherein the other blocks consist of polybutadiene, polyethylene butylene, polyisoprene and polyisoprene/butadiene copolymer. Examples of such S-TPEs are polystyrene-butadiene-polystyrene (SBS), polystyrene-polyethylene-butylene-polystyrene (SEBS), polystyrene-polyisoprene-polystyrene (SEPS), polystyrene-polyisoprene/butadiene-polystyrene (SEEPS) and polymethyl-methacrylate-polybutadiene-polystyrene (MBS) block copolymers. However, even a block, for example the polybutadiene block in SBS, can be replaced by a statistical styrene-butadiene copolymer. The S-TPEs of the present invention are thus not limited to pure block copolymers.

Copolyesters are formed when polyesters are modified, which are in turn combinations of diacids and diols. As an example, the well-known polyethylene terephthalate (PET), which is produced from terephthalic acid (TPS) and ethylene glycol (EG), can become another copolyester, such as e.g. polycyclohexylenedimethylene terephthalate (TPS+CHDM/EG) by the integration of other monomers, such as isophthalic acid (IPA) or cyclohexanedimethanol (CHDM). Copolyesters usually have good properties with regard to strength, transparency and other mechanical properties, such as excellent tenacity, hydrolytic stability, heat resistance and resistance to chemicals, which normally influence polymers such as e.g. polycarbonate. A polyester used in this invention is Tritan MX710 from the Eastman company, which possesses the properties cited above.

Copolyester ethers comprise a polyester segment and a polyether segment. Copolyester ethers have good properties such as transparency, tenacity and high chemical resistance. Here the polyester segment is composed as described above, i.e. it can be a polyester like PET or a corresponding copolyester. The polyether fragment consists of a polyether (also polyalkylene glycol, polyether polyol, polyalkylene oxide) or of a polyether polyol. Examples of polyethers are polyethylene glycol (PEG) and polypropylene glycol (PPG), which are both produced by catalytic polymerization of the corresponding epoxies (oxiranes) ethylene oxide and propylene oxide. The corresponding polyether polyols can be produced by conversion of epoxies using diols. As well as diols, polyvalent alcohols such as e.g. glycerine, 1,1,1-trimethylolpropane (TMP), pentaerythritol or sorbitol can be converted with epoxies in the presence of strong bases (e.g. KOH) to polyether polyols. The polyether fragment can also be present as a block copolymer, which is produced by sequential polymerization with different epoxides. Common polyether polyols are Lupranol (BASF SE) and Desmophen (Bayer Material Science). Epoxy resins are also polyethers with terminal epoxy groups. However, the preferred copolyester ethers in this invention are those that are composed of a simple polyester and a simple polyether. One example of such a copolyester ether used in this invention is Ecdel 9967 by Eastman.

Cyclic olefin copolymers (COC) are copolymers with olefin units such as ethylene and cyclic olefin units such as e.g. norbornene. Norbornene is produced, for example, from cyclopentadiene and ethylene. The reaction to the copolymer is usually metallocene catalyzed and leads to statistical copolymers. Although only consisting of olefins, COCs are amorphous in contrast to the semi-crystalline polyolefins such as polyethylene and polypropylene and are thus transparent. The properties of COC can be changed in a wide range by changing the integration ratios of cyclic and linear olefins. For example, the bulky norbornene, when used, suppresses crystallinity and leads to rigid polymer chains. However, flexible amorphous copolymers can be obtained by a low norbornene content of less than 20 mol %. Flexible semi-crystalline copolymers can be obtained by a low norbornene content of less than 15 mol %. The heat resistance can basically be adjusted in a range of 65 to 190° C. What is common to all COCs is a range of properties such as good thermoplastic flowability, high stiffness, strength and hardness as well as low density and high transparency with good acid and alkali resistance. A cyclic olefin copolymer used in this invention is the TOPAS elastomer E-140 from Topas Advanced Polymers.

If S-TPE, copolyester, copolyester ether or cyclic olefin copolymer are used for the layer, they give the tube good connectability, in particular a good bonding capability with the materials that are typically used to produce medical containers and connectors attached thereto, such as ABS, PC, PVC, PMMA, copolyester, copolyester ether, thermoplastic polyurethane (TPU) or mixtures of these substances.

With a suitable choice of the material of the other layer, for example EVA, a tube of this kind is also no more expensive to manufacture than tubes of PVC with plasticizers. In addition, the EVA can also be mixed (blend) with a TPE (e.g. SEBS copolymer) to improve its recovery behavior. Such a tube is also free of PVC and plasticizers and due to this is environmentally compatible in disposal and is not hazardous to health or carcinogenic.

The tube preferably contains at least one layer which contains an ethylene-vinyl acetate copolymer (EVA). In particular, this one layer is not the layer that contains the styrene-containing thermoplastic polymer, copolyester, copolyester ether or cyclic olefin copolymer. A tube with a layer containing an S-TPE, copolyester, copolyester ether or cyclic olefin copolymer and a layer containing EVA is no more expensive to manufacture than conventionally used tubes of PVC with plasticizers and is free from PVC and plasticizers.

The vinyl acetate (VA) portion of the ethylene-vinyl acetate copolymer is 10% to 30 wt %, preferably 14% to 28%. Due to this material selection, the tube is immune to temperature changes and has good mechanical properties, such as good recovery behavior.

In the embodiment in which at least one layer contains ethylene-vinyl acetate copolymer (EVA), this layer can (additionally) contain a transparent thermoplastic polybutene or optionally an SEBS. The thermoplastic polybutene or SEBS can be added in the layer as an additive with a proportion of 1 wt % to 50 wt %, preferably 10 wt % to 20 wt %.

The tube can be formed so that the outer of the at least two layers contains a styrene-containing thermoplastic polymer (e.g. Styroflex 2G 66 of the manufacturer Styrolution), a copolyester (e.g. Tritan MX710 of the manufacturer Eastman), a copolyester ether (e.g. Ecdel 9967 of the manufacturer Eastman) or a cyclic olefin copolymer (e.g. Topas® elastomer from Topas Advanced Materials). Such a tube is adapted for connection to a medical container according to the second connection type, i.e. for insertion into a connector of the medical container formed as an adaptor piece.

Alternatively to this, the tube can be formed so that the inner of the at least two layers contains a styrene-containing thermoplastic polymer, a copolyester, a copolyester ether or a cyclic olefin copolymer. Such a tube is adapted for connection to a medical container according to the first connection type, i.e. for pushing the tube onto a connector of the medical container formed in the shape of a cone.

The layer containing the styrene-containing thermoplastic copolymer, copolyester, copolyester ether or cyclic olefin copolymer preferably has a thickness that is smaller than the thickness of the other layer of the at least two layers of the tube. With a suitable choice of material of the other layer, for example EVA, the tube has good mechanical properties, in particular good elasticity. Furthermore, the comparatively thinner layer containing the polystyrene-containing thermoplastic polymer, copolyester, copolyester ether or cyclic olefin copolymer is well adapted for bonding between this layer and materials that are typically used to produce medical containers or connectors provided thereon, such as acrylonitrile butadiene styrene (ABS), polycarbonate (PC), polyvinyl chloride (PVC), polymethyl methacrylate (PMMA), copolyester, copolyester ether, thermoplastic polyurethane (TPU) or combinations of these materials.

Alternatively to a two-layer structure, the tube wall can also consist of at least three layers, wherein the outer and the inner of the at least three layers contain a styrene-containing thermoplastic polymer, copolyester, copolyester ether or cyclic olefin copolymer. A tube formed in this way is adapted for bonding both with a connector formed as an adaptor piece and formed cone-shaped. A tube formed in this way can also be used as an adaptor piece for connecting the ends of two tubes of different diameters or for connecting one tube to a connector formed cone-shaped, wherein the outer diameter of the connector is smaller than the inner diameter of the tube, or for connecting a tube to a connector formed as an adaptor piece, wherein the inner diameter of the connector is greater than the outer diameter of the tube.

In the tube comprising at least three layers, the outer and the inner layer containing the styrene-containing thermoplastic polymer, copolyester, copolyester ether or cyclic olefin copolymer can each have a thickness that is smaller than the thickness of the middle layer of the at least three layers. The advantages achieved by this are the same as for the tube with a two-layer wall structure and a layer containing S-TPE that is thinner compared with the thickness of the other layer.

The layer containing the styrene-containing thermoplastic polymer, copolyester, copolyester ether or cyclic olefin copolymer can have a thickness of 0.01 to 0.3 mm. A small thickness of this kind is sufficient to provide a good bonding capability by means of the S-TPE contained in the layer. Moreover, the starting material requirement (raw material requirement) of the S-TPE is small compared with that of the material of the other, relatively thicker layer of the tube.

The tube can have an inner diameter of 3.0 mm and with a tolerance of ±0.1 mm. Such a tube is adapted for use with connectors formed in the shape of a cone that are commercially available and standardized with regard to their size, in particular the outer diameter.

The tube can have an outer diameter of 4.10 mm with a tolerance of +0.1 mm and −0.3 mm. Such a tube is adapted for use with commercially available and standardized connectors formed as adaptor pieces.

The tube can have a wall thickness of 0.55 mm with a tolerance of ±0.05 mm. A tube formed in this way has similarly advantageous mechanical properties as the tubes of PVC with plasticizers that are in widespread use and are in particular standardized.

The tube can be produced by coextrusion. The tube is thus manufactured in a one-stage and thus economical manufacturing process.

According to another aspect of the present invention, a medical container is provided, in particular a container for enteral or parenteral nutrition. According to the invention, the medical container comprises at least one attachment of an inventive tube as described above.

The container can be produced from a material that contains ethylene-vinyl acetate copolymer (EVA), and the attachment can be welded to an outer layer of the tube, of which the outer of the at least two layers contains the styrene-containing thermoplastic polymer, copolyester, copolyester ether or cyclic olefin copolymer.

Alternatively the medical container can be produced from a material that contains ethylene-vinyl acetate copolymer (EVA), wherein the container comprises an attachment formed in the shape of a cone, onto which a tube with an inner layer, which contains a styrene-containing thermoplastic polymer, copolyester, copolyester ether or cyclic olefin copolymer has been pushed.

Figure 2:
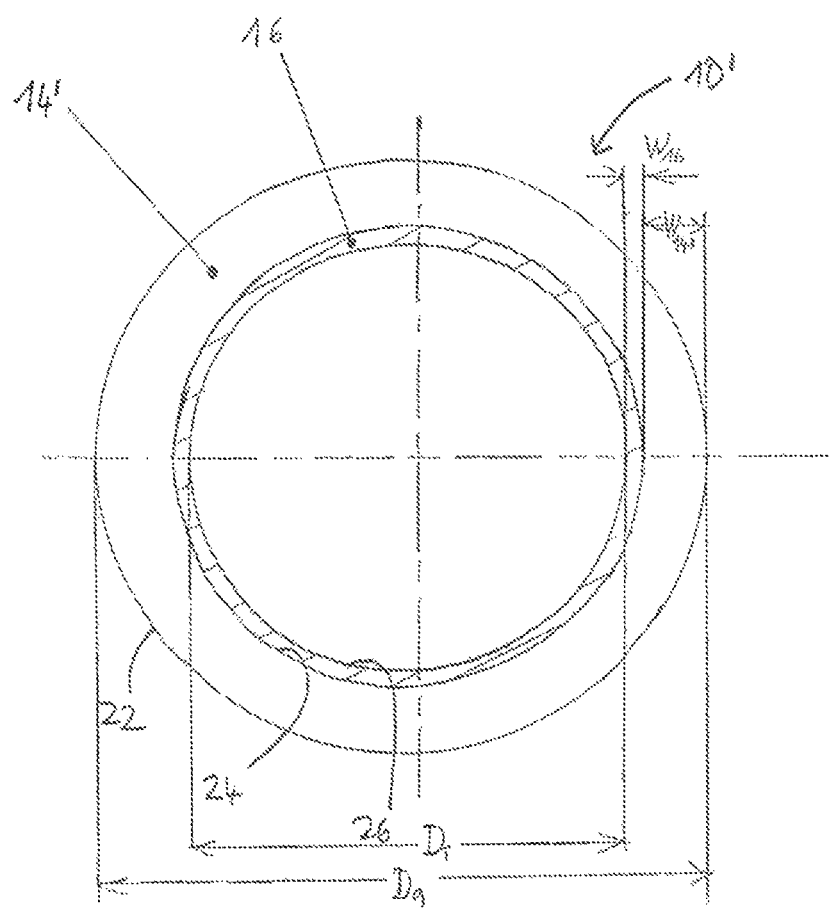
Figure 3:
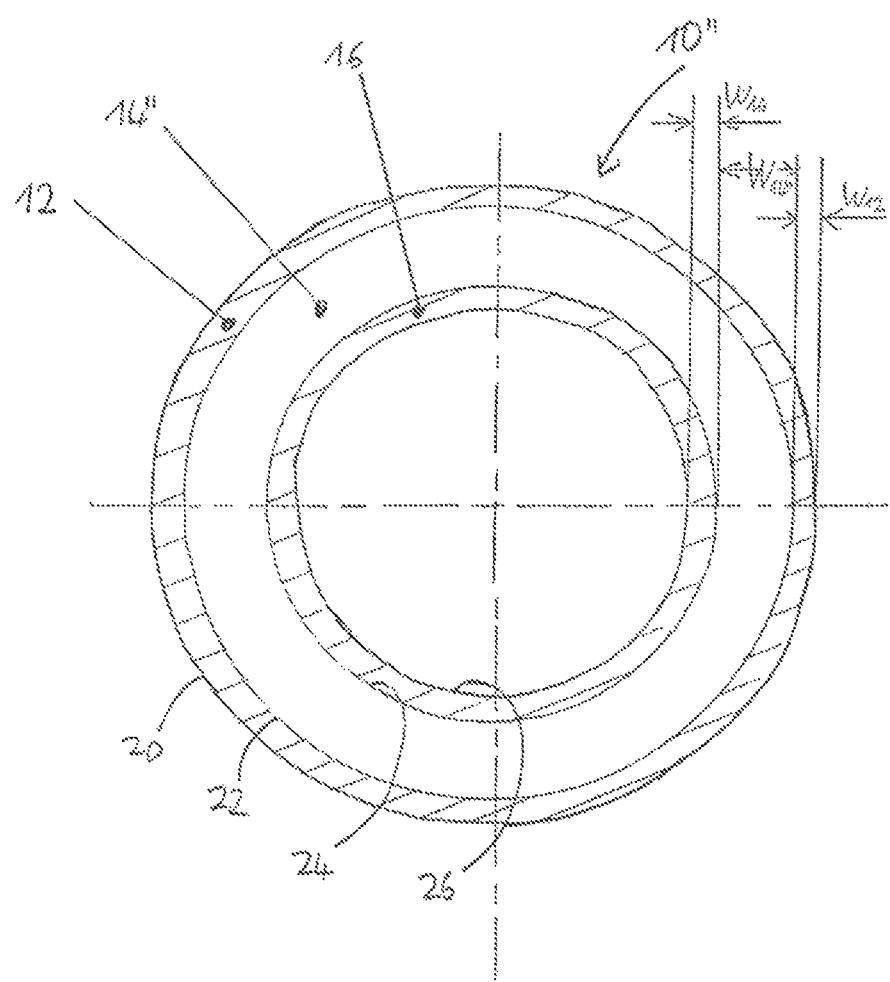

In the following, two exemplary embodiments of the invention are described in greater detail with reference to the drawings. These show:

FIG. 1 a cross section through a first embodiment of a tube according to the invention;

FIG. 2 a cross section through a second embodiment of a tube according to the invention, and FIG. 3 a cross section through a third embodiment of a tube according to the invention.

In FIGS. 1 and 2, a tube 10 and a tube 10' are respectively shown with a two-layer structure of the tube wall. The tube 10 according to the first embodiment of the invention shown in FIG. 1 comprises an outer layer 12, which contains a styrene-containing thermoplastic polymer, copolyester, copolyester ether or cyclic olefin copolymer, and an inner layer 14, which contains a material different from the material of the outer layer 12. The outer layer 12 can also be produced completely from a styrene-containing thermoplastic polymer, such as a styrene-butadiene block copolymer (SBC), a copolyester, a copolyester ether or a cyclic olefin copolymer. The inner layer 14 is produced from a material different from polyvinyl chloride (PVC) and from polycarbonate (PC) and is produced advantageously from ethylene-vinyl acetate (EVA) with a vinyl portion of 10 wt % to 30 wt %, preferably 14 wt % to 28 wt %.

The tube 10' according to the second embodiment of the invention shown in FIG. 2 comprises an outer layer 14', which is produced from a material different from PVC, from PC and from S-TPE, and an inner layer 16, which contains a styrene-containing thermoplastic polymer, copolyester, copolyester ether or cyclic olefin copolymer. What was said regarding the materials contained in the outer layer 12 and the inner layer 14 of the tube 10 in FIG. 1 applies correspondingly to the materials contained in the inner layer 16 and the outer layer 14' of the tube 10' in FIG. 2.

The outer layers (layer 12 in FIG. 1 and layer 14' in FIG. 2) and the inner layers (layer 14 in FIG. 1 and layer 16 in FIG. 2) each have a uniform wall thickness. An outer surface of a respective inner layer of the tubes 10 in FIGS. 1 and 10' in FIG. 2 is in full contact with an inner surface of the respective outer layer.

The outer surface and an inner surface of the respective inner layer as well as an outer surface and the inner surface of the respective outer layer each have a circular cross section. Furthermore, they are arranged coaxially, thus with coincident center points in cross section. The tubes 10 (in FIGS. 1) and 10' (in FIG. 2) are each produced by co-extrusion, so that the respective outer layer and the respective inner layer are fixedly connected to one another. The respective tube 10 and 10' is sterilized at least on the inner surface 24 and 26 of the respective inner layer 14 and 16 of the tube 10 and 10' and preferably also on the outer surface 20 and 22 of the respective outer layer 12 and 14', for example by treatment with ethylene oxide or by radiation sterilization.

The tube 10" according to the third embodiment of the invention shown in FIG. 3 has a tube wall with a three-layer structure. The tube wall comprises an outer layer 12, which contains a styrene-containing thermoplastic polymer, copolyester, copolyester ether or a cyclic olefin copolymer, a middle layer 14", which contains a material different from PVC, PC and S-TPE, and an inner layer 16, which contains a styrene-containing thermoplastic polymer, copolyester, copolyester ether or a cyclic olefin copolymer. With regard to the materials of the outer layer 12 and the inner layer 16, the same applies as was said regarding the outer layer 12 of the tube 10 in FIG. 1 and the inner layer 16 of the tube 10' in FIG. 2. With regard to the material of the middle layer 14" of the tube 10" in FIG. 3, the same applies as was said regarding the material of the inner layer 14 of the tube 10 shown in FIG. 1 and the material of the outer layer 14' of the tube 10' shown in FIG. 2.

In a preferred embodiment, the product available under the brand name Styroflex® with the product designation 2G 66 from the company BASF is preferably used as the styrene-containing thermoplastic polymer (S-TPE). In another preferred embodiment, the product available from the Eastman company with the product designation Tritan MX710 or alternatively the copolyester ether with the product designation Ecdel 9967 by Eastman is used as copolyester. In another preferred embodiment, the COC Topas® elastomer from Topas Advanced Materials is used as cyclic olefin copolymer.

In the embodiments of a tube, in which the at least one layer contains an ethylene-vinyl acetate copolymer (EVA), a transparent thermoplastic polybutene (e.g. the product designated Koattro KT AR05 of the manufacturer Basell) or SEBS (e.g. Kraton G1652 from the manufacturer Kraton) can also be added in the production of this layer. The weight percentage of the polybutene or SEBS here can be 1% to 50%, preferably 10% to 20%, more preferably 2% and even more preferably 5%.

In series of tests it was found that, by adding a thermoplastic polybutene or SEBS as an additive to the EVA, generally
    the susceptibility to kinking is reduced;
    the properties of the tube in respect of its bending characteristics (including the "snap") become more similar to those of a tube made from PVC, which is desirable, because in the professional world tubes made from PVC are regarded as standard and new developments of medical tubes are compared with tubes made from PVC;
    the elasticity improves, so that the tube can be wound more easily (which is advantageous, because the tube is wound for transportation in several (O-shaped) windings onto storage and transport spools);
    and finally a pronounced "shape memory" (technically termed "memory") of tubes made from EVA (i.e. EVA without any additive) is reduced (which occurs, for example, when using a new (fresh) tube on account of the bending radius of a spool used in transportation).

The outer layer 12, the middle layer 14" and the inner layer 16 each have a uniform wall thickness. An outer surface of the inner layer 16 is fully in contact with an inner surface 24 of the middle layer 14" and an outer surface 22 of the middle layer 14" is fully in contact with an inner surface of the outer layer 12. The outer surfaces and the inner surfaces of an inner, middle and outer layer respectively have a circular cross section. They are arranged coaxially, thus with center points coincident with the cross section. The tube 10" is produced by co-extrusion, so that the outer layer 12 is fixedly connected to the middle layer 14" and the inner layer 16 is fixedly connected to the middle layer 14". The tube 10" is sterilized on the inner surface 26 of the inner layer 16 and preferably also on the outer surface 20 of the outer layer 12, for example by treatment with ethylene oxide or by radiation sterilization.

In the tubes 10, 10', 10" according to the first to third embodiment of the invention shown in FIGS. 1 to 3, the inner diameter $D_i$ is 3.0 mm with a tolerance of ±0.10 mm, the outer diameter $D_a$ is 4.10 mm with a tolerance of +0.10 mm and −0.30 mm and the wall thickness $W_{12}$, $W_{16}$ of the S-TPE-containing layers 12, 16 is 0.01 to 0.30 mm.

An infusion device, not shown in the figures, comprises a medical container and a medical connection tube to the patient. The medical container has a bag with a connector for connection of a medical tube. The bag consists of ethylene-vinyl acetate copolymer and is filled with a nutritional solution containing fat, for example for the enteral or parenteral nutrition of a patient.

In one embodiment, the container comprises a connector formed as an inlet socket. The container is produced from ethylene-vinyl acetate copolymer and the connector from acrylonitrile-butadiene-styrene (ABS), polycarbonate (PC), polyvinyl chloride (PVC), polymethyl methacrylate (PMMA), copolyester, copolyester ether, thermoplastic polyurethane (TPU) or combinations of these. The connector is formed as an inlet socket, into which a medical tube can be introduced or plugged. The tube is formed according to the first embodiment shown in FIG. 1 or according to the third embodiment shown in FIG. 3 and has a layer 12 containing S-TPE on its outside. The layer 12 of the tube 10 or 10" is bonded with the inside of the inlet socket, namely using a commercially available solvent such as cyclohexanone (CHEX), tetrahydrofuran (THF), methyl ethyl ketone (MEK) or a mixture of these substances (e.g. MIX-MEK/CHEX).

In another embodiment, the connector is formed cone-shaped and a tube 10' according to the second embodiment shown in FIG. 2 or a tube 10" according to the third embodiment of the medical tube according to the invention shown in FIG. 3 is pushed over the cone-shaped connector.

Prior to pushing it on, a commercially available solvent is applied to the inner surface of the tube 10, 10' or/and to the outer surface of the cone-shaped connector and acts as a lubricant when pushing the tube onto the connector. After the tube has been pushed onto the connector, the tube is elongated in its longitudinal direction, at least in the region pushed onto the connector, so that an elastic tension directed radially inwards or a contact pressure directed radially inwards is created on the outer surface of the cone-shaped connector. Under the influence of the solvent, the inner layer 16 of the tube 10' or 10" and the outer surface of the cone-shaped connector are dissolved and fixedly bonded to one another by adhesion.

To produce the tubes 10, 10', 10" according to the first, second and third embodiment, a co-extrusion machine is supplied with the two raw materials ethylene-vinyl acetate copolymer or alternatively a polymer blend of EVA and thermoplastic polybutene or/and SEBS as solids, and the outer and/or inner layer of styrene-containing thermoplastic polymer (e.g. Styroflex 2G 66 from the manufacturer Styrolution), copolyester (e.g. Tritan MX710 of the manufacturer Eastman), copolyester ether (e.g. Ecdel 9967 of the manufacturer Eastman) or cyclic olefin copolymer (e.g. Topas® elastomer from Topas Advanced Materials) in particular as granulate, separately from one another. The raw materials are heated separately and each compressed by an extruder device, for example a barrel extruder. The heated and viscous masses are supplied separately to a suitably designed extrusion nozzle, from which they emerge in the first embodiment as tube 10 with an inner layer of EVA and an outer layer of S-TPE, copolyester, copolyester ether or COC, in the second embodiment as tube 10' with an outer layer 14' of EVA and an inner layer 16 of S-TPE and in the third embodiment as tube 10" with an outer layer 12 and an inner layer 16 of S-TPE, copolyester, copolyester ether or COC and a middle layer 14" of EVA.

Experimental Part

The materials described in the application for the tubes for connection to a medical container were tested on the basis of adhesion tests and their bending stiffness and were compared with one another.

Determining the Bending Stiffness

In this series of tests, the deflection or elasticity of the tubes at a given load was determined. A FRANK-PTI bending stiffness tester TS was used for this purpose.

In the tests below (see table 1), tubes with the materials and material combinations indicated below were used.

In test series 1, PVC was tested. The PVC used was soft PVC with a hardness of Shore A 80, the plasticizer was DINCH from BASF SE.

In test series 2, LDPE/S-TPE was used as a two-layer tube material. The LDPE used was Purell PE 1840 from the manufacturer Basell, the S-TPE was Styroflex 2G 66 from the manufacturer Styrolution.

In test series 3, EVA/copolyester ether was used as two-layer tube material. The EVA used was Evathane 28.05 from the manufacturer ARKEMA, while the copolyester ether was Ecdel 9967 from Eastman.

In test series 4, EVA/PET was used as two-layer tube material.

In test series 5, soft PP was used as the tube material. The soft PP used was a blend of random polypropylene copolymer and a hydrated styrene/isoprene block copolymer.

In test series 6, EVA alone was used as tube material.

The materials commonly used in medical technology, hard PVC (Nakan RMA705N T01, reference), polycarbonate (Makrolon Rx 1805) and copolyester (Tritan MX 731), were tested as connectors in the test series.

For each test series, 10 tubes of approx. 10 cm in length were tested. The test was carried out after 72 h storage in an air-conditioned environment in analogy with the ShoreA test (ISO 868). The samples were clamped in the intended clamping device provided, wherein the tube projected approx. 1 cm from the rear of the clamping device and the greater part of the tube projected at the front.

The test conditions or parameter setting were as follows:
23° C.±1° C. room temperature
Measuring accuracy ±1%
Test velocity 6°/s
Velocity to pre-load: 6°/s
Angle: 30° (indication of final angle)
Dwell time: 2 s
Pre-load: 0.005 N
Test spacing: 30 mm The measuring results were read as measured maximum force [N] and repeated until 10 measuring results were obtained, from which the mean value was formed.

Determining the Pull-Off Force by Tensile Testing

In this series of tests, the pull-off force in [N] was determined by tensile testing.

The tube materials used were the same as for determination of the bending stiffness.

The different tubes were each bonded using the solvents described (tetrahydrofuran (THF) or mixture of methyl ethyl ketone (MEK) and cyclohexanone (CH or CHEX) with the various molded parts and were stored prior to the tensile tests for 5 days at room temperature until the solvents had evaporated completely.

The test samples in this case were the various molded parts, which were bonded to a tube. A tensile testing machine from the Zwick company was used as the measuring apparatus.

The test velocity was 200 mm/min, while the clamping length was specific to the sample.

Results

EN 1615/1618 refers to an adequate tensile strength when this comes to 15 N. However, this is considered too low here. It was therefore attempted in the present case to achieve a tensile strength of at least 2× this standard, hence of at least 30 N.

A material has adequate adhesive properties e.g. if a pull-off force of at least around 35 N is required. A pull-off force lower than this of 20 N, for example, indicates inadequate stability of the tube-connector bond.

A material has good elasticity if it has a bending stiffness of below approx. 0.7 mN. Materials with a higher bending stiffness are normally too rigid and not suitable for use as a tube for medical containers.

It was found that although the PVC normally used has good adhesive properties, it is much too hard and moreover, as described at the beginning, has other disadvantages, such as e.g. plasticizers contained therein and a lack of environmental compatibility (see tables 1 and 2, test series 1).

If a tube of transparent EVA (monotube) is used, on the other hand, the grip on the connector is inadequate, as proved to be the case in the adhesion tests (see table 1, test series 7).

The use of soft PP also turned out to be inadequate with regard to the adhesive properties (see table 1, test series 6).

In addition, different material combinations were compared with one another. Although the combination of LDPE and styrene-containing thermoplastic polymer (Styroflex 2G 66) leads to good adhesive properties (see table 1, test series 2), it leads to insufficient flexibility (see table 2, test series 2).

The combinations of
EVA with a copolyester ether (tables 1 and 2, test series 3), of
EVA with a styrene-containing thermoplastic polymer (tables 1 and 2, test series 4), and of
EVA with a copolyester (tables 1 and 2, test series 5)
all have good elastic properties and at the same time exhibit a good bonding capability with the materials of connectors.

Thermoplastic polybutene and/or SEBS can also be used instead of EVA.

It was thus shown with reference to the tests that the tubes according to the invention with at least two layers, wherein one layer consists of S-TPE, copolyester or copolyester ether, satisfy the desired properties of good bonding capability and high elasticity. The cyclic olefin copolymers have also demonstrated the desired properties in experiments not shown here.

REFERENCE SIGN LIST

10 Tube
10' Tube
10" Tube
12 Outer layer of S-TPE
14 Layer of EVA
14' Layer of EVA
14" Layer of EVA
16 Inner layer of S-TPE
20 Outer surface (of the outer layer 12)
22 Outer surface (of the layer 14, 14', 14")
24 Inner surface (of the layer 14, 14', 14")
26 Inner surface (of the inner layer 16)
$D_i$ Inner diameter
$D_a$ Outer diameter
$W_{12}$ Thickness of layer 12
$W_{14}$ Thickness of layer 14
$W_{14}'$ Thickness of layer 14'
$W_{14}"$ Thickness of layer 14"
$W_{16}$ Thickness of layer 16

TABLE 1

Adhesive tests with different single-layer and two-layer tubes

| Sample Designation Tube | Dimension | Tube material | Connector | Solvent | Pull-off force (N) | Type of pull-off |
|---|---|---|---|---|---|---|
| Test series 1 | 3 × 4.1 | PVC | Hard PVC | THF | 86.1 | Tube tears in connector |
|  | 3 × 4.1 | PVC | Hard PVC | 50T MEK/50T CH | 80.1 | Tube tears at connector |
|  | 3 × 4.1 | PVC | Polycarbonate | THF | 51.4 | Tube pulls off |
|  | 3 × 4.1 | PVC | Polycarbonate | 50T MEK/50T CH | 51.8 | Tube pulls off |
|  | 3 × 4.1 | PVC | Copolyester | THF | 81.2 | Tube tears at connector |
|  | 3 × 4.1 | PVC | Copolyester | 50T MEK/50T CH | 64.0 | Tube tears in connector |
| Test series 2 | 3/0.65 | LDPE/S-TPE | Polycarbonate | THF | 81.7 | Tube pulls off |
|  | 3/0.65 | LDPE/S-TPE | Polycarbonate | 50T MEK/50T CH | 72.6 | Tube pulls off |
|  | 3/0.65 | LDPE/S-TPE | Copolyester | THF | 72.5 | Tube pulls off |
|  | 3/0.65 | LDPE/S-TPE | Copolyester | 50T MEK/50T CH | 80.6 | Tube pulls off |
| Test series 3 | 0.65 × 4.15 | EVA/Copolyester ether | Hard PVC | THF | 46.6 | Tube pulls off |
|  | 0.65 × 4.15 | EVA/Copolyester ether | Hard PVC | 50T MEK/50T CH | 54.3 | Tube tears at connector |
|  | 0.65 × 4.15 | EVA/Copolyester ether | Polycarbonate | THF | 45.0 | Tube tears at connector |
|  | 0.65 × 4.15 | EVA/Copolyester ether | Polycarbonate | 50T MEK/50T CH | 40.5 | Tube pulls off |
|  | 0.65 × 4.15 | EVA/Copolyester ether | Copolyester | THF | 35.1 | Tube pulls off |
|  | 0.65 × 4.15 | EVA/Copolyester ether | Copolyester | 50T MEK/50T CH | 27.9 | Tube pulls off |
| Test series 4 | 3/0.65 | EVA/S-TPE | Polycarbonate | THF | 36.6 | Tube pulls off |
|  | 3/0.65 | EVA/S-TPE | Polycarbonate | 50T MEK/50T CH | 40.5 | Tube pulls off |
|  | 3/0.65 | EVA/S-TPE | Copolyester | THF | 37.8 | Tube pulls off |
|  | 3/0.65 | EVA/S-TPE | Copolyester | 50T MEK/50T CH | 59.6 | Tube pulls off |
| Test series 5 | 0.65/4.15 | EVA/Copolyester | Polycarbonate | THF | 27.5 | Tube tears off at connector |
|  | 0.65/4.15 | EVA/Copolyester | Copolyester | THF | 33.2 | Tube tears off at connector |
|  | 0.65/4.15 | EVA/Copolyester | Copolyester | 50T MEK/50T CH | 28.2 | Tube tears off at connector |
| Test series 6 | 3 × 4.16 | Soft PP | Polycarbonate | THF | 21.5 | Tube tears off |
|  | 3 × 4.16 | Soft PP | Copolyester | THF | 20.4 | Tube tears off at connector |
|  | 3 × 4.16 | Soft PP | Copolyester | 50T MEK/50T CH | 24.4 | Tube tears off |
| Test series 7 | 2.98 × 4.18 | EVA | Polycarbonate | THF | 29.1 | Tube tears off |
|  | 2.98 × 4.18 | EVA | Copolyester | THF | 23.4 | Tube tears off |
|  | 2.98 × 4.18 | EVA | Copolyester | 50T MEK/50T CH | 15.7 | Tube tears off |

TABLE 2

Measurement of bending stiffness of different single-layer and two-layer tubes

|  | Material | Bending stiffness (mN) |
|---|---|---|
| Test series 1 | PVC | 0.120 |
| Test series 2 | LDPE/S-TPE | 0.713 |
| Test series 3 | EVA/Copolyester ether | 0.308 |
| Test series 4 | EVA/S-TPE | 0.246 |
| Test series 5 | EVA/Copolyester | 1.206 |

The invention claimed is:

1. A tube for connection to a medical container with a tube wall, which consists of at least two layers that elastically recover after compression, comprising:
   a first layer that contains a styrene-containing thermoplastic polymer, copolyester, copolyester ether, or cyclic olefin copolymer, and
   a second layer that contains ethylene-vinyl acetate copolymer (EVA) blended with an additive of a transparent thermoplastic polybutene and/or polystyrene-polyethylene-butylene-polystyrene (SEBS), wherein the second layer containing the EVA is thicker than the first layer and the first layer is connected to the medical container, wherein the styrene-containing thermoplastic polymer is selected from styrene-butadiene block copolymer (SBC), polystyrene-polybutadiene-polystyrene (SBS), polystyrene-polyisoprene-polystyrene (SEPS), polystyrene-isoprene/butadiene-polystyrene (SEEPS), and polymethyl-methacrylate-polybutadiene-polystyrene (MBS) block copolymer.

2. The tube according to claim 1, wherein the vinyl acetate (VA) weight portion of the ethylene-vinyl acetate copolymer (EVA) is 10% to 30%.

3. The tube according to claim 1, wherein the first layer is an outermost layer of the tube.

4. The tube according claim 1, wherein the first layer is an innermost layer of the tube and the second layer does not contain styrene-containing thermoplastic polymer, copolyester, copolyester ether, or cyclic olefin copolymer.

5. The tube according to claim 1,
wherein the tube wall includes a third layer, the first layer is an inner layer within the second layer, and the third layer is an outer layer that overlies the second layer, wherein the third layer contains styrene-containing thermoplastic polymer (S-TPE), copolyester, copolyester ether, or cyclic olefin copolymer, and wherein the first and third layers each have a thickness that is smaller than the thickness of the second layer.

6. The tube according to claim 1, wherein the first layer has a thickness of 0.01 to 0.30 mm.

7. The tube according to claim 1, wherein the tube has an inner diameter of 1.0 to 6.0 mm with a tolerance of ±0.1 mm.

8. The tube according to claim 1, wherein the tube has a total wall thickness of 0.3 to 1.0 mm with a tolerance of ±0.05 mm.

9. A medical container, in particular for enteral or parenteral nutrition, which further comprises the attachment of a tube according to claim 1.

10. The medical container according to claim 9, wherein the material from which the container is manufactured contains ethylene-vinyl acetate copolymer (EVA) and the container has a connector formed as an adaptor piece, wherein a tube according to claim 4 is plugged into the adaptor piece, and wherein the inside of the adaptor piece in particular is welded or bonded to the first layer of the tube.

11. The medical container according to claim 9,
wherein the material from which the container is manufactured contains ethylene-vinyl acetate copolymer (EVA) and the container includes as an attachment a cone-shaped connector, onto which a tube according to claim 5 is pushed, wherein the outside in particular of the cone-shaped connector is welded or bonded to the first layer of the tube.

12. The tube according to claim 2, wherein the first layer is an outermost layer of the tube and the second layer does not contain styrene-containing thermoplastic polymer, copolyester, copolyester ether, or cyclic olefin copolymer.

13. The tube according to claim 1, wherein the first layer and the second layer each include a bending stiffness of below 0.7 mN.

14. The tube according to claim 1, wherein the thermoplastic polybutene and/or SEBS is added to the second layer during production.

15. The tube according to claim 2, wherein the first layer is an innermost layer of the tube and the second layer does not contain styrene-containing thermoplastic polymer, copolyester, copolyester ether, or cyclic olefin copolymer.

16. The tube according to claim 1, wherein the styrene-containing thermoplastic polymer is polymethyl-methacrylate-polybutadiene-polystyrene (MBS) block copolymer.

17. The tube according to claim 1, wherein the tube has an outer diameter of 2.0 to 8.0 mm with a tolerance of ±0.05 mm.

18. A tube for connection to a medical container with a tube wall, which consists of at least two layers that elastically recover after compression, comprising:
a first layer that contains a styrene-containing thermoplastic polymer, copolyester, copolyester ether, or cyclic olefin copolymer, and a second layer that contains ethylene-vinyl acetate copolymer (EVA) blended with an additive of a transparent thermoplastic polybutene and/or polystyrene-polyethylene-butylene-polystyrene (SEBS), wherein the second layer containing the EVA is thicker than the first layer and the first layer is an outer layer that overlies the second layer for connection of the first layer to the medical container, wherein the styrene-containing thermoplastic polymer is selected from styrene-butadiene block copolymer (SBC), polystyrene-polybutadiene-polystyrene (SBS), polystyrene-polyisoprene-polystyrene (SEPS), polystyrene-isoprene/butadiene-polystyrene (SEEPS), and polymethyl-methacrylate-polybutadiene-polystyrene (MBS) block copolymer.

19. A tube for connection to a medical container with a tube wall, which consists of at least two layers that elastically recover after compression, comprising:
a first layer for connection to the medical container that contains a styrene-containing thermoplastic polymer, copolyester, copolyester ether, or cyclic olefin copolymer, and a second layer that contains ethylene-vinyl acetate copolymer (EVA) blended with an additive of a transparent thermoplastic polybutene and/or polystyrene-polyethylene-butylene-polystyrene (SEBS), wherein the second layer containing the EVA is thicker than the first layer and the second layer does not contain styrene-containing thermoplastic polymer, copolyester, copolyester ether, or cyclic olefin copolymer, wherein the styrene-containing thermoplastic polymer is selected from styrene-butadiene block copolymer (SBC), polystyrene-polybutadiene-polystyrene (SBS), polystyrene-polyisoprene-polystyrene (SEPS), polystyrene-isoprene/butadiene-polystyrene (SEEPS), and polymethyl-methacrylate-polybutadiene-polystyrene (MBS) block copolymer.

20. The tube according to claim 1, wherein a weight percentage of the additive is selected from one of the following: 1%, 5%, and 10% to 20%.

* * * * *